(12) United States Patent
Leach

(10) Patent No.: US 9,713,327 B2
(45) Date of Patent: Jul. 25, 2017

(54) CELL WASHING DEVICE USING NON-MECHANICAL FLUID VORTEX FLOW

(71) Applicant: Biomet Biologics, LLC, Warsaw, IN (US)

(72) Inventor: Michael D. Leach, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 334 days.

(21) Appl. No.: 14/220,635

(22) Filed: Mar. 20, 2014

(65) Prior Publication Data

US 2015/0264917 A1   Sep. 24, 2015

(51) Int. Cl.
    *A01N 1/02* (2006.01)
    *A61M 1/02* (2006.01)
    *A47J 43/07* (2006.01)

(52) U.S. Cl.
    CPC ............. *A01N 1/02* (2013.01); *A61M 1/0281* (2013.01); *A61M 2206/16* (2013.01)

(58) Field of Classification Search
    CPC ..................................................... B05B 1/207
    See application file for complete search history.

(56) References Cited

U.S. PATENT DOCUMENTS

| | | | | |
|---|---|---|---|---|
| 2,099,317 | A | * | 11/1937 | Schmiedeknecht .... A61C 17/14 4/263 |
| 4,191,182 | A | | 3/1980 | Popovich et al. |
| 4,509,545 | A | * | 4/1985 | Trotter .................... A47J 43/24 134/199 |
| 4,911,833 | A | | 3/1990 | Schoendorfer et al. |
| 4,935,002 | A | | 6/1990 | Gordon |
| 5,216,760 | A | * | 6/1993 | Brown ................... A47K 13/08 4/245.4 |
| D340,983 | S | | 11/1993 | Spielberg |
| 5,771,792 | A | * | 6/1998 | Chen ....................... A47J 43/24 134/115 R |
| 6,960,178 | B2 | | 11/2005 | Chang et al. |
| 7,314,460 | B2 | | 1/2008 | Tu et al. |

(Continued)

FOREIGN PATENT DOCUMENTS

| | | |
|---|---|---|
| CN | 2204802 Y | 8/1995 |
| EP | 0097455 A2 | 1/1984 |

(Continued)

OTHER PUBLICATIONS

"International Application Serial No. PCT/US2015/021499, International Search Report mailed Jul. 23, 2015", 3 pgs.

(Continued)

*Primary Examiner* — Krishnan S Menon
*Assistant Examiner* — Bradley R Spies
(74) *Attorney, Agent, or Firm* — Schwegman Lundberg & Woessner, P.A.

(57) ABSTRACT

A device for washing a suspension of cells. The device includes a bowl-shaped basin having a top end and a bottom end and an axis extending from the top end to the bottom end, and an inlet port formed in the basin. The inlet port is positioned at an angle to allow for a wash solution to be injected or delivered into the basin and circulate around the basin about the central axis. A suspension of cells can be washed in the circulating wash solution. The circulating wash solution forces the cells to settle at the bottom of the basin, where they can be extracted.

24 Claims, 15 Drawing Sheets

(56) References Cited

U.S. PATENT DOCUMENTS

| | | |
|---|---|---|
| 7,470,245 B2 | 12/2008 | Tu et al. |
| 8,016,736 B2 | 9/2011 | Hlavinka et al. |
| 8,337,711 B2 | 12/2012 | Dorian et al. |
| 2001/0020601 A1* | 9/2001 | Gabele ............... A61L 2/26 210/348 |
| 2003/0164328 A1* | 9/2003 | Arnaud ............ B01D 21/2433 210/512.1 |
| 2007/0056092 A1* | 3/2007 | Prather ............... E03C 1/18 4/619 |
| 2011/0003675 A1 | 1/2011 | Dolecek |
| 2013/0184685 A1 | 7/2013 | Buffet et al. |
| 2014/0047986 A1 | 2/2014 | Robinson |
| 2014/0050615 A1* | 2/2014 | Robinson ............... B30B 9/04 422/44 |

FOREIGN PATENT DOCUMENTS

| | | |
|---|---|---|
| WO | WO-2010030589 A2 | 3/2010 |
| WO | WO-2015143176 A1 | 9/2015 |

OTHER PUBLICATIONS

"International Application Serial No. PCT/US2015/021499, Written Opinion mailed Jul. 23, 2015", 6 pgs.

"European Application Serial No. 15720229.2, Response filed May 22, 2017 to Action mailed Nov. 10, 2016", 15 pgs.

\* cited by examiner

CELL WASHING DEVICE USING NON-MECHANICAL FLUID VORTEX FLOW

BACKGROUND

This section provides background information related to the present disclosure which is not necessarily prior art.

Blood transfusions are used to treat many disorders and injuries, such as in the treatment of accident victims and during surgical procedures. According to current American Red Cross statistics, about 5 million people receive blood transfusions each year, in the United States alone. Thus, health care systems rely on the collection and distribution of blood. Typically, blood is obtained from a donor and then processed and stored; units of stored blood or blood products are then taken from storage as needed and transfused into a patient in need. In some cases, the blood may be an autologous donation, where an individual donates blood in expectation of receiving his or her own blood by transfusion during a medical procedure.

Donated blood is typically processed into components and then placed in storage until needed. When a subject is in need of a blood transfusion, a unit of blood is commonly removed from storage, rejuvenated, washed, and resuspended in an appropriate solution. In some instances, the red blood cells were lyophilized prior to storage, in which case they need to be resuspended, washed, and then resuspended again in an appropriate solution. The resuspended red blood cells are then transfused into the subject. In either scenario, washing the red blood cells is traditionally a tedious, time consuming and multistep process that requires a great deal of tubing, and the use of expensive centrifuges with rotating seals to separate the cells from the wash solution.

Although traditional methods for washing blood are effective, there remains a need to develop devices and processes for washing blood that are less complicated and that reduce the amount of tubing required for the process. Eliminating the need for a rotating seal and centrifugal force for washing blood would also be desirable.

SUMMARY

This section provides a general summary of the disclosure, and is not a comprehensive disclosure of its full scope or all of its features.

The present technology provides a device for washing a suspension of cells, such as a suspension of whole blood or a suspension of red blood cells. The devices can include a bowl-shaped basin having an inner surface, an outer surface, a top end, a bottom end, and a central axis extending from the top end to the bottom end. The device can further include an inlet port formed into the basin that is positioned at an angle that allows for a wash solution to be injected or delivered into the basin and circulate around the basin about the central axis. Circulating wash solution results in a vortex, which forces cells to the bottom end of the basin. Therefore, cellular suspensions can be washed in the circulating wash solution, wherein the vortex forces the cells to settle at the bottom end of the basin, where they can be extracted. The device can be used to wash cells without extensive amounts of tubing and without the use of mechanical means, such as centrifugation.

The present technology also provides a device for washing red blood cells. The device includes:

a. a substantially bowl-shaped wash basin that has an open top end, a bottom end, and an annular reservoir, the annular reservoir having a plurality of angled apertures;

b. an annular lid including a filter, wherein the annular lid is in contact with and covers the reservoir, and the filter covers the open top end of the wash basin;

c. a first angled inlet port for introducing a wash solution into the reservoir, wherein the angle of the inlet port directs wash solution to flow around the reservoir and through the angled apertures to generate a vortex of wash solution in the basin; and d. a second inlet port for introducing the red blood cells into the wash basin, wherein the second inlet is positioned below the annular reservoir.

The present technology further provides a method for washing a suspension of cells. The method comprises:

a. continuously delivering a wash solution through a first inlet port to allow the wash solution to flow in a circular motion that results in a vortex;

b. injecting a suspension of cells through a second inlet port, wherein the cells are dispersed in the wash solution and then settle at a bottom of the wash basin; and c. extracting the cells.

Extracting can include one of selecting a syringe having a barrel, a plunger, and a cannula; inserting the cannula into the cells at the bottom of the wash basin; and drawing back the plunger to aspirate the cells into the syringe barrel, or drawing the cells out of the wash basin through an outlet port.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6 is a perspective view of a lid assembly for the first device for washing a suspension of cells, wherein the lid assembly comprises a lower lid unit, an upper lid unit, and a filter positioned there between;

Corresponding reference numerals indicate corresponding parts throughout the several views of the drawings.

DETAILED DESCRIPTION

Figure 1:
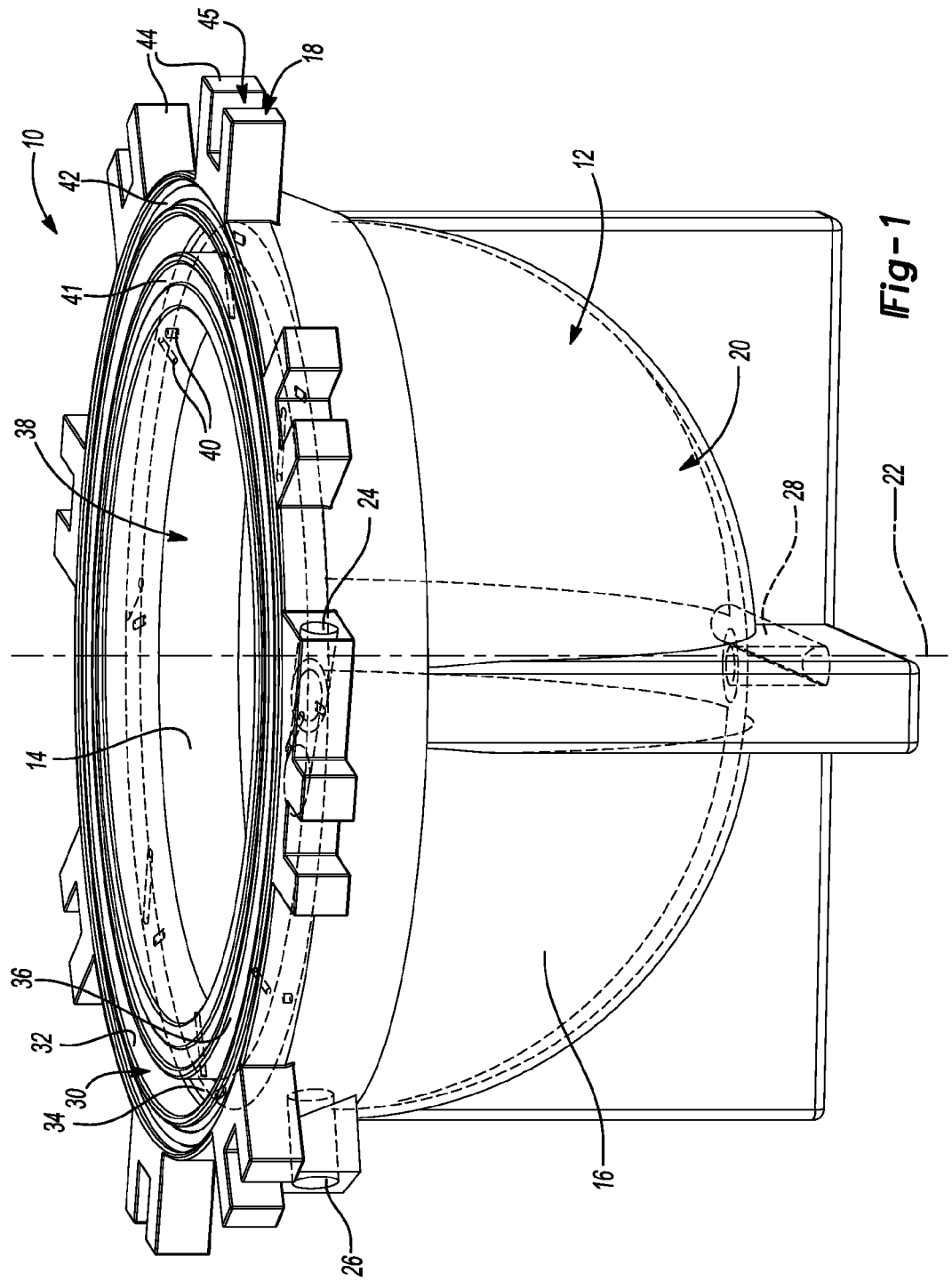
FIG. 1 is a first perspective of a first device for washing a suspension of cells.
Figure 2:
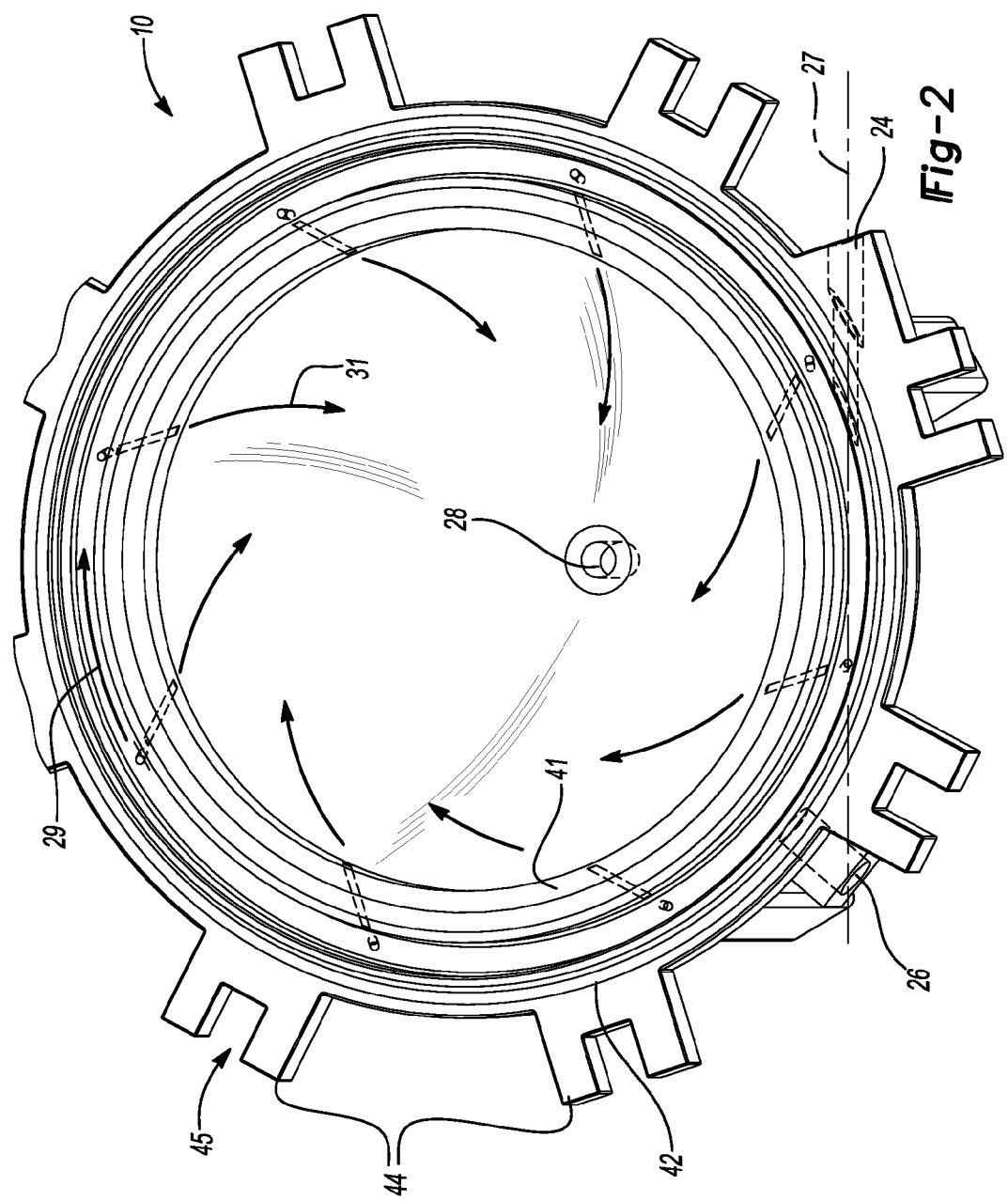
FIG. 2 is a second perspective of the first device for washing a suspension of cells.
Figure 3:
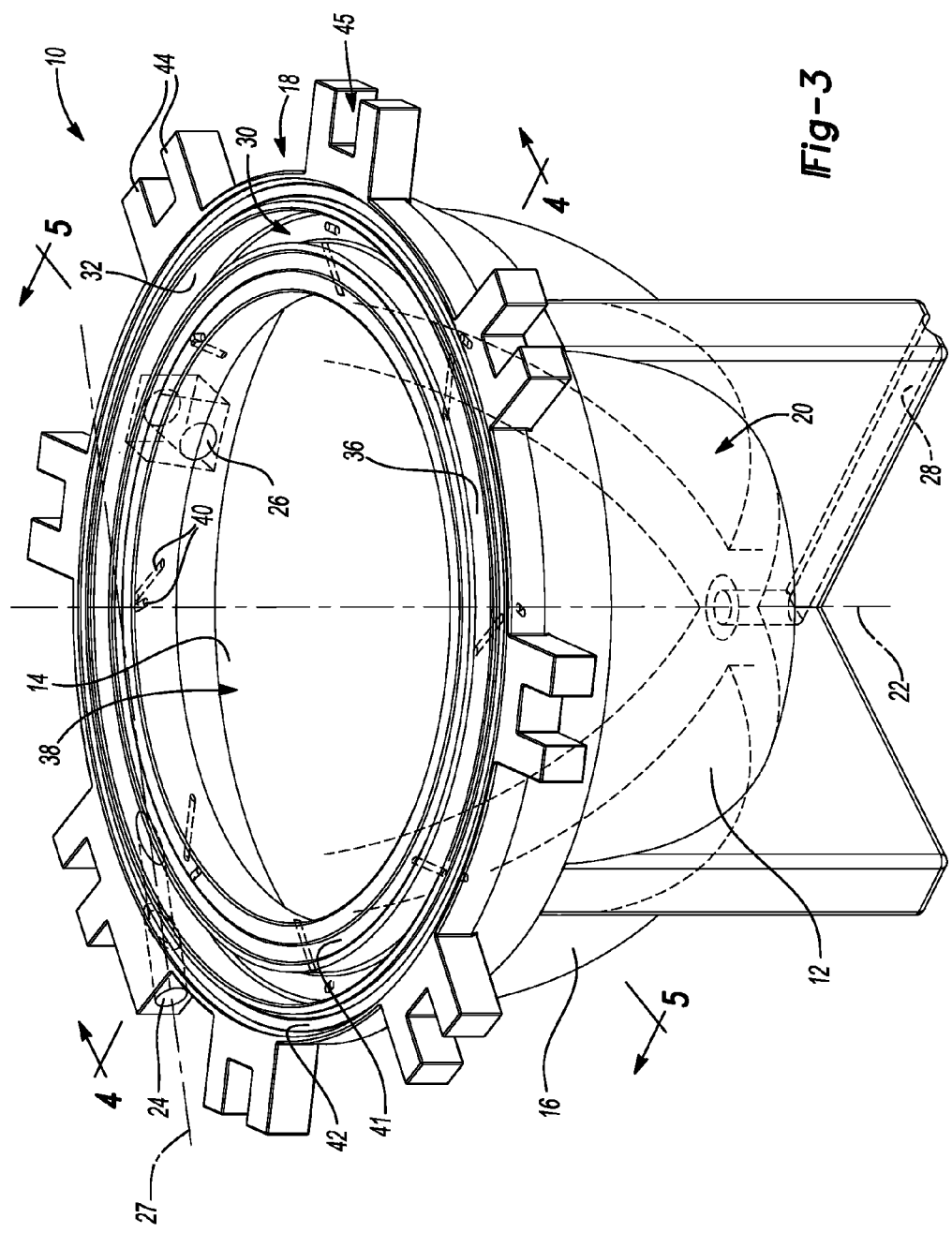
FIG. 3 is a third perspective of the first device for washing a suspension of cells.

Example embodiments will now be described more fully with reference to the accompanying drawings.

The present technology generally provides devices and methods for washing suspensions of cells by non-mechanical means. The devices and methods rely on a circular flow of wash solution, which causes a vortex, to wash suspensions of cells, without the use of, for example, a centrifuge. Accordingly, the devices according to the present technology do not comprise moving parts and do not require centrifugal force.

The device can be used to wash cell suspensions comprising any type of cell that requires washing. Non-limiting examples of cell suspensions include whole blood, fractions of whole blood, a suspension of red blood cells, a suspension of adipocytes, and a suspension of chondrocytes. Cell suspensions can also comprise cells that were harvested or isolated from a piece of tissue or organ and then suspended. Moreover, the cells can be harvested or isolated from any animal, such as a human or non-human mammal. Therefore, in various embodiments, the cells are red blood cells harvested from a human subject. The red blood cells can be fresh, i.e. harvested from a human subject at a time proximate to washing in the device. For example, fresh red blood cells may be harvested from a donor at a time of 5 minutes, 15 minutes, 30 minutes, 45 minutes, 1 hour, 2 hours, or 3 hours prior to the time of washing. In some embodiments, the red blood cells were harvested at a time prior to washing and stored for a period of time. Therefore, the cell suspension can be obtained from storage, or stored lyophilized cells can be suspended in a solution to generate a suspension of cells.

The device is suitable to wash a suspension of cells with any wash solution commonly used in the art. Non-limiting examples of wash solutions include saline, phosphate buffered saline (PBS), dextrose, water, and combinations thereof.

With reference to FIGS. 1-5, the present teachings provide a device 10 for washing a suspension of cells. The device 10 comprises a bowl-shaped basin 12 having an inner semi-spherical surface 14, an outer semi-spherical surface 16, a top end 18, a bottom end 20, and a central axis 22 extending from the top end 18 to the bottom end 20. In various embodiments, the inner surface 14 defines a shape that is conical, spherical, or any other shape that promotes a circular fluid path. In some embodiments, the bottom end 20 of the basin 12 is curved, pointed, or flat. The inner surface 14 and outer surface 16 define a first circular opening 38. The device 10 further comprises a first inlet port 24 at the top end 18 of the basin 12. The inlet port 24 extends along a plane that is perpendicular to the axis 22 and extends along a second axis 27 that passes through a portion of the perimeter of the top end 18 of the device 10. The angle allows for a wash solution to be injected or delivered through the first inlet port 24 and to circulate around the basin 12 about the central axis 22 as shown by arrow 29 so that a circular flow of the wash solution forms about the central axis 22 as shown by arrows 31. The wash solution can be injected or delivered by gravity feed or under pressure, for example, with the use of a pump. The circulating wash solution results in a vortex, which forces particulate matter, such as cells, to settle at the bottom end 20 of the basin 12. The device 10 further comprises a second inlet port 26, which is positioned lower on the basin 12 than the first angled inlet port 24 and generally perpendicular to axis 22 and intersecting axis 22. A suspension of cells can be injected or delivered into the wash solution that is circulating around the inner surface 14 of the basin 12 through the second inlet port 26. In some embodiments, the bottom end 20 of the basin comprises an extraction port 28, through which wash cells can be extracted when a wash is complete.

Figure 4:
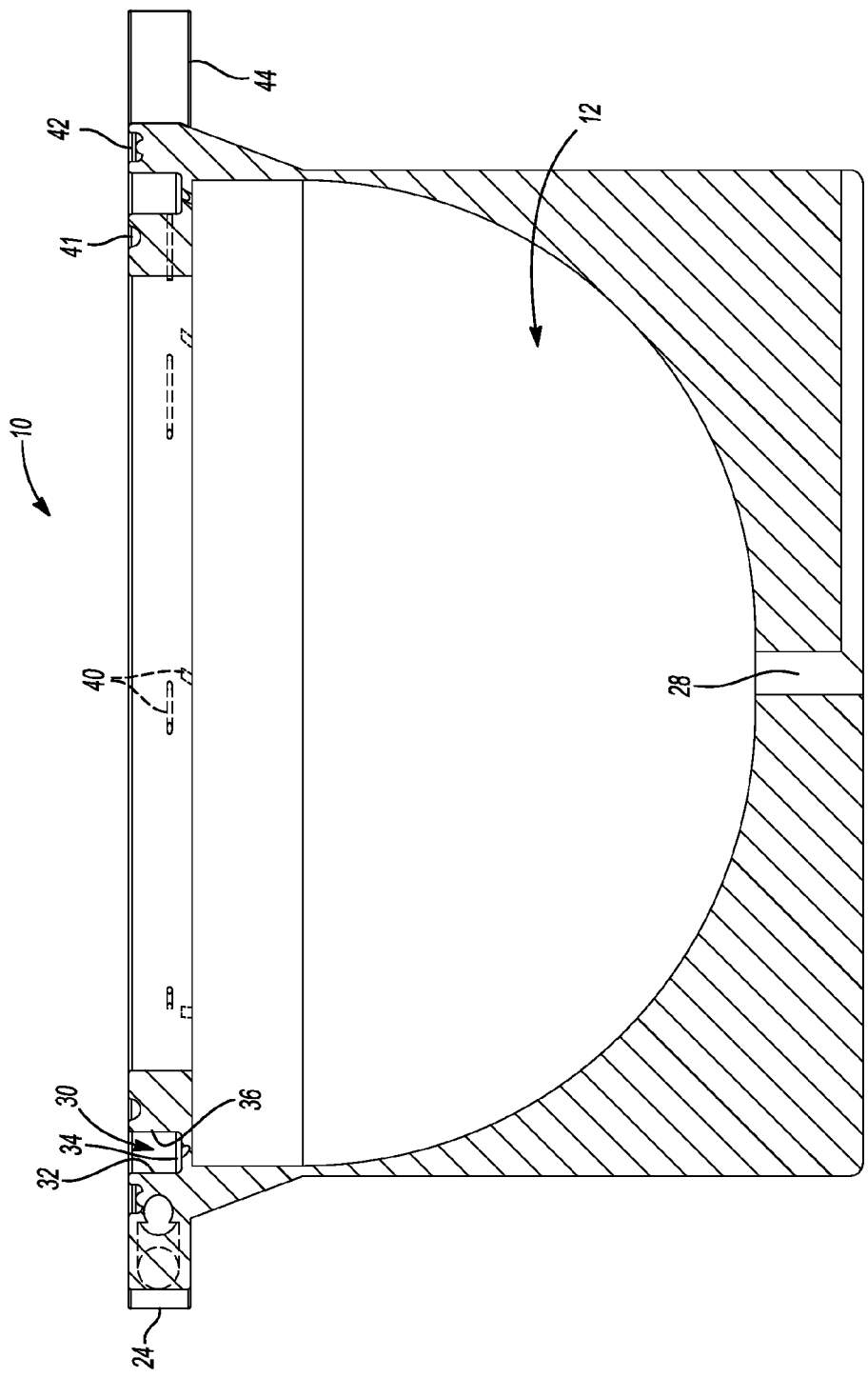
FIG. 4 is a cross section of the first device along line 4 of FIG. 3 for washing a suspension of cells in a first perspective.
Figure 5:
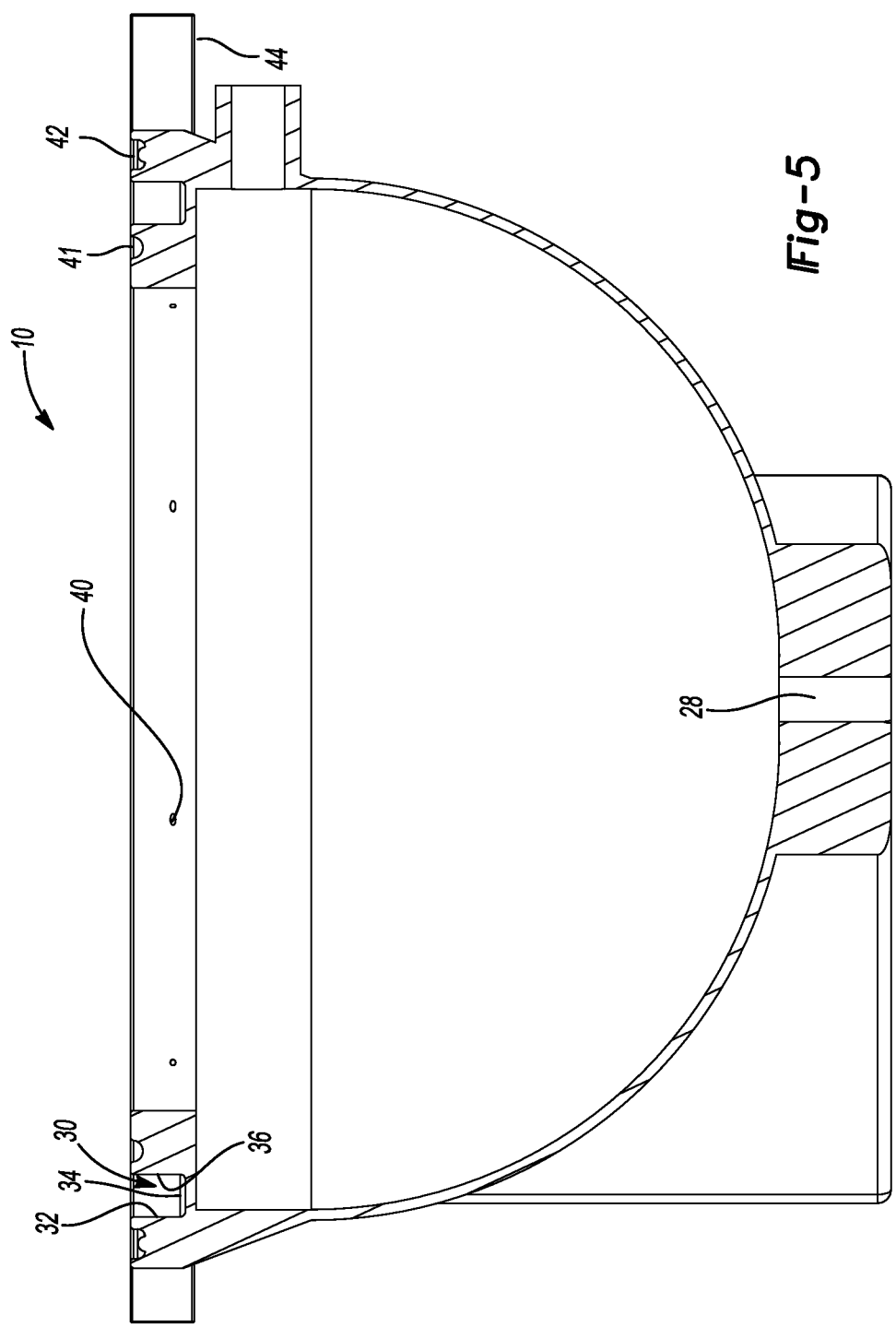
FIG. 5 is a cross section of the first device along line 5 of FIG. 3 for washing a suspension of cells in a second perspective.

The top end 18 of the inner surface 14 of the device 10 comprises an annular reservoir 30. The annular reservoir 30 comprises an outer edge or wall 32 and a bottom surface 34 and an inner edge or wall 36. The outer edge 32 of the reservoir 30 comprises the inner surface 14 of the basin 12. The first inlet port 24 is positioned so that injected or delivered wash solution circulates around the reservoir 30. The second inlet port 26 is positioned below the reservoir 30, so cells injected or delivered thought he second inlet port 26 enter the basin 12 of the device 10, and not the reservoir 30. The inner edge 36 of the reservoir 30 defines a first circular opening 38. FIGS. 4-5 are cross sectional views of the device 10, which show the reservoir 30 in detail. As shown in FIGS. 1-4, both the bottom surface 34 and the inner edge 36 of the reservoir 30 comprise a plurality of angled apertures 40. The angled apertures 40 are positioned such that they promote circular flow of the wash solution into the wash basin 12 from the reservoir 30. In other words, the direction of flow of the apertures 40 matches that of the direction of flow of the inlet 24 (i.e. a clockwise flow). However, in various embodiments, a device is configured as a mirror image as the device 10, in which flow is directed in a counter-clockwise direction through an inlet port, reservoir and a plurality of apertures passing through the reservoir. Although the figures show the angled apertures 40 in both the bottom surface 34 and inner edge 36 of the reservoir 30, in alternative embodiments, the apertures 40 are located only in the bottom surface 34 of the of the reservoir 30 or only in the inner edge 36 of the reservoir 30. In various embodiments, the device 10 comprises from about 2 angled apertures 40 to about 50 angled apertures 40 positioned radially about the reservoir 30. The top end 18 of the inner edge 36 and the outer edge 32 of the device 10 comprise a first inner annular groove 41 and a second outer annular groove 42, respectively, for accepting concentric O-rings. Additionally, a plurality of first tabs 44 extend radially outwardly from the top end 18 of the outer surface 16 of the device 10 and are used to secure a lid assembly to the device as further discussed herein. As shown in the FIG. 3, the first tabs 44 can define a U-shaped recess or opening 45.

Figure 6:
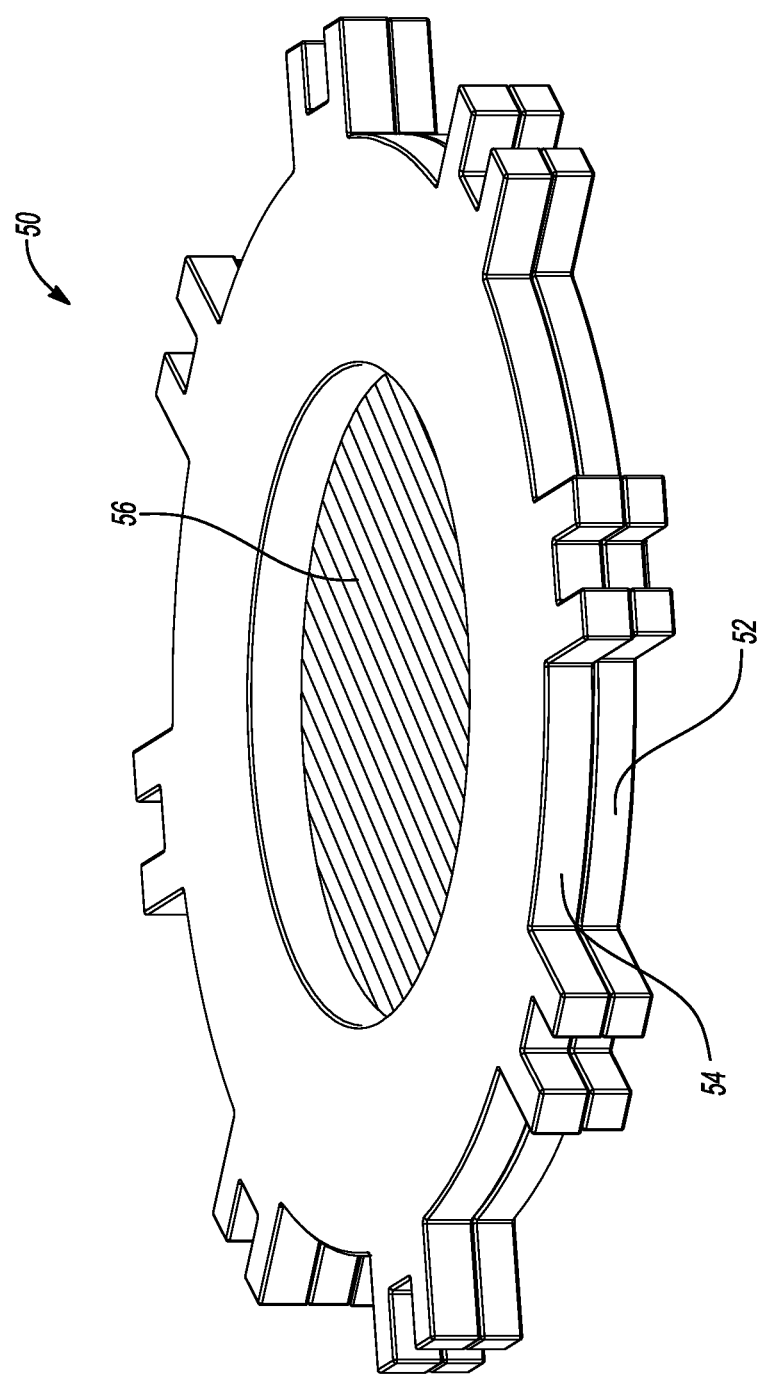

As shown in FIG. 6, the device 10 further comprises a lid assembly 50. The lid assembly 50 comprises an annular lower unit 52, an annular upper unit 54, and a disc-shaped filter 56 positioned between the lower unit 52 and the upper unit 54.

Figure 7:
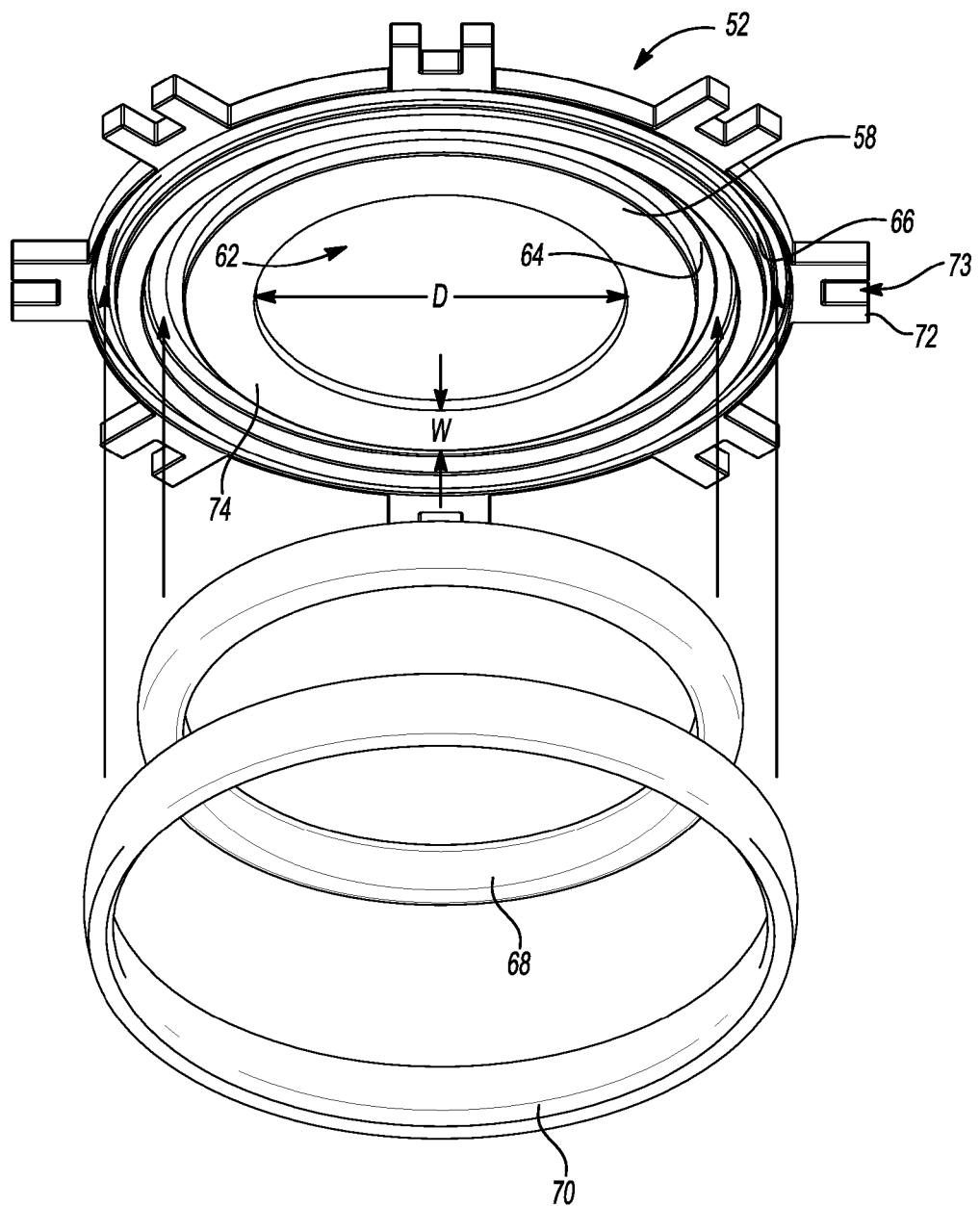
FIG. 7 is an exploded perspective view of a bottom surface of the lower lid unit.
Figure 8:
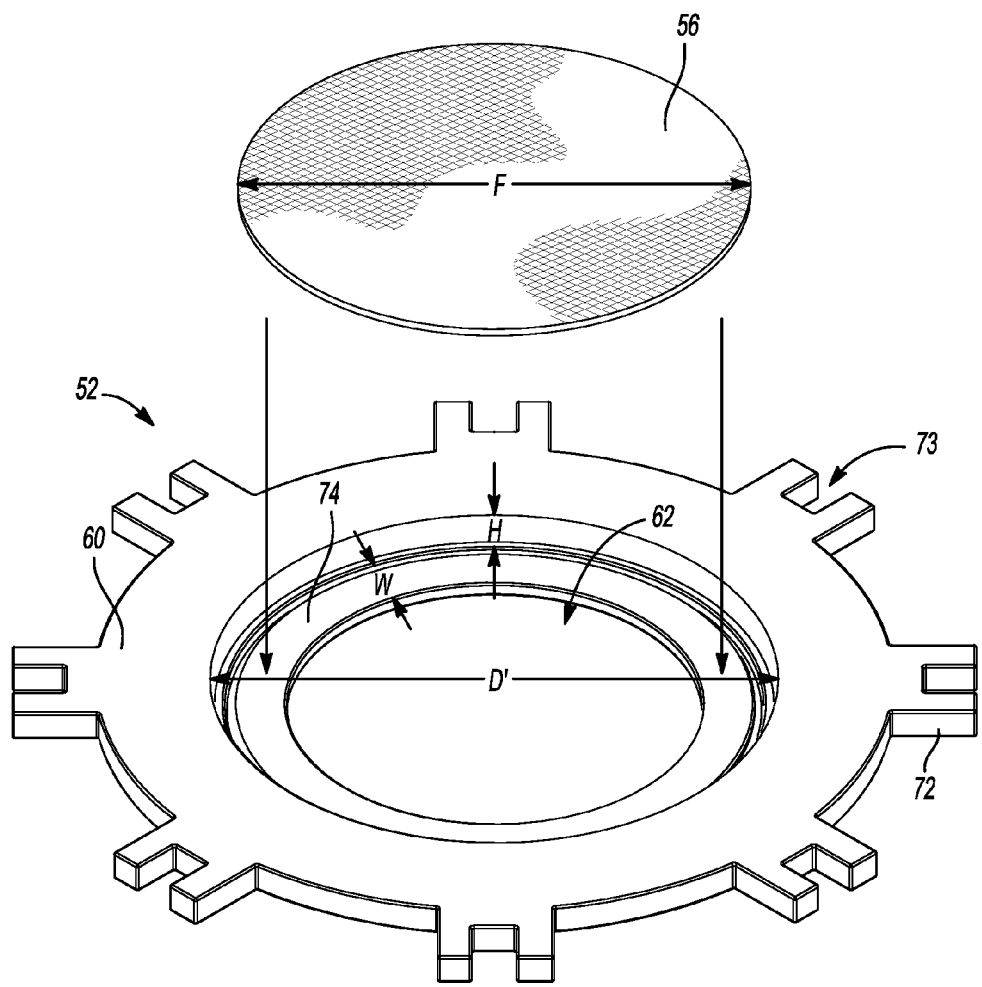
FIG. 8 is a perspective view of a top surface of the lower lid unit and the filter.

The annular lower unit 52 is shown in greater detail in FIGS. 7-8. The annular lower unit 52 comprises a first bottom surface 58 and a first top surface 60 that define a second circular opening 62. The first top surface 60 is substantially flat. The first bottom surface 58 of the lower unit 52 comprises an annular inner third groove 64 and an annular outer fourth groove 66 for accepting a first O-ring 68 and a second O-ring 70, respectively. The third groove 64 and the fourth groove 66 are concentric about axis 22. Additionally, a plurality of second tabs 72 extend radially outwardly from the lower unit 52 and are used to secure the lower unit 52 to the device 10. The second tabs 72 can define a U-shaped recess or opening 73. When the lower unit 52 is positioned over the device 10, the first 68 and second 70 O-rings fit into the first groove 41 and the second groove 42, respectively, and the second tabs 72 of the lower unit 52 align with the first tabs 44 of the device 10.

Additionally, the bottom surface 58 of the lower unit 52 extends partially into the second circular opening 62 to form an annular ledge or a shelf 74 with respect to the top surface 60 of the lower unit 52. The ledge/shelf 74 has a width W. The second circular opening 62 has a diameter D with respect to the bottom surface 58. The top surface 60 of the lower unit 52 does not project into the second circular opening 62. Therefore, the second circular opening 62 has a diameter D' with respect to the top surface 60. Consequently diameter D is smaller than diameter D' by a difference of 2 W. The ledge/shelf 74 has a height H, as shown in FIG. 8. The filter 56 has a diameter F, which is substantially similar to the diameter D' of the second circular opening 62. Accordingly, the filter 56 can be positioned on the ledge/shelf 74 to completely cover the second circular opening 62. The filter 56 has a pore size that allows the wash solution to pass through, but retains cells in the device 10.

Figure 9:
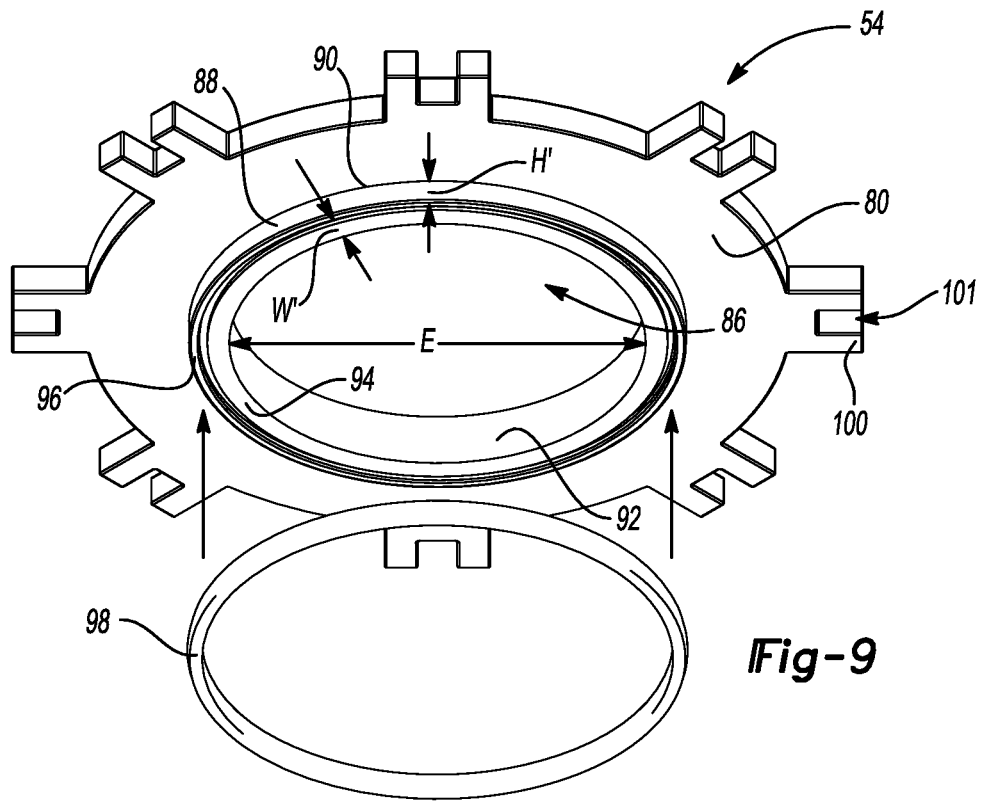
FIG. 9 is an exploded perspective view of a bottom surface of the upper lid unit.
Figure 10:
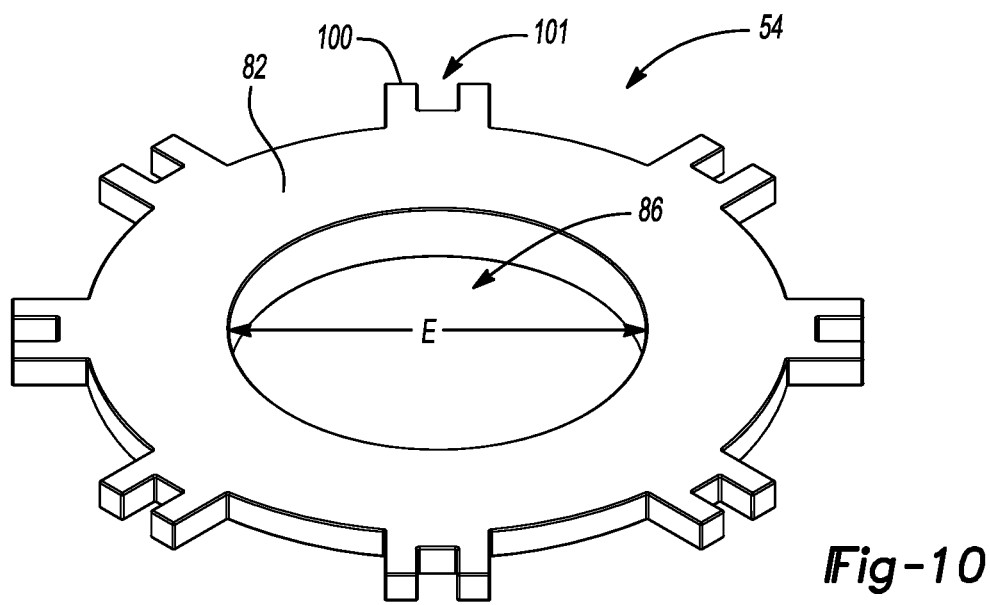
FIG. 10 is a perspective view of a top surface of the upper lid unit.

The annular upper unit 54 of the lid assembly 50 is shown in detail in FIGS. 9-10. The annular upper unit 54 comprises a second bottom surface 80 and a second top surface 82 that define a third circular opening 86. The third circular opening 86 has a diameter E, which is substantially similar to diameter D of the second circular opening 62 of the lower unit 52. The second bottom surface 80 of the upper unit 54 comprises an annular shoulder 88 that projects outward from the second bottom surface 80 around the third circular opening 86. The shoulder 88 comprises an outer shoulder edge or wall 90, an inner shoulder edge or wall 92, and a flat shoulder surface 94. The outer shoulder edge 90 has a height H', which is substantially similar to the height H of the ledge/shelf 74 of the lower unit 52. The flat shoulder surface 94 has a width W', which is substantially similar to the width W of the ledge/shelf 74 of the lower unit 52. Additionally, the flat shoulder surface 94 comprises a fifth annular groove 96, which accepts a third O-ring 98. The upper unit 54 further comprises a plurality of third tabs 100 that extend radially outwardly from the upper unit 54 and are used to secure the upper unit 54 to the lower unit 52. The third tabs 100 can also define a U-shaped recess or opening 101 that align with the corresponding U-shaped openings 73, 45 of the lower unit 52 and device 10. Therefore, the third tabs 100 align with the second tabs 72 of the lower unit 52, which align with the first tabs 44 of the device.

The upper lid unit 54 can be positioned on top of lower lid unit 52, with the shoulder 88 of the upper unit 54 fitting in the second circular opening 62 of the lower unit 52 and resting on the ledge/shelf 74. The filter 56 is captured between the ledge/shelf 74 of the lower unit 52 and the flat shoulder surface 94 of the shoulder 88 of the upper unit 54.

Figure 11:
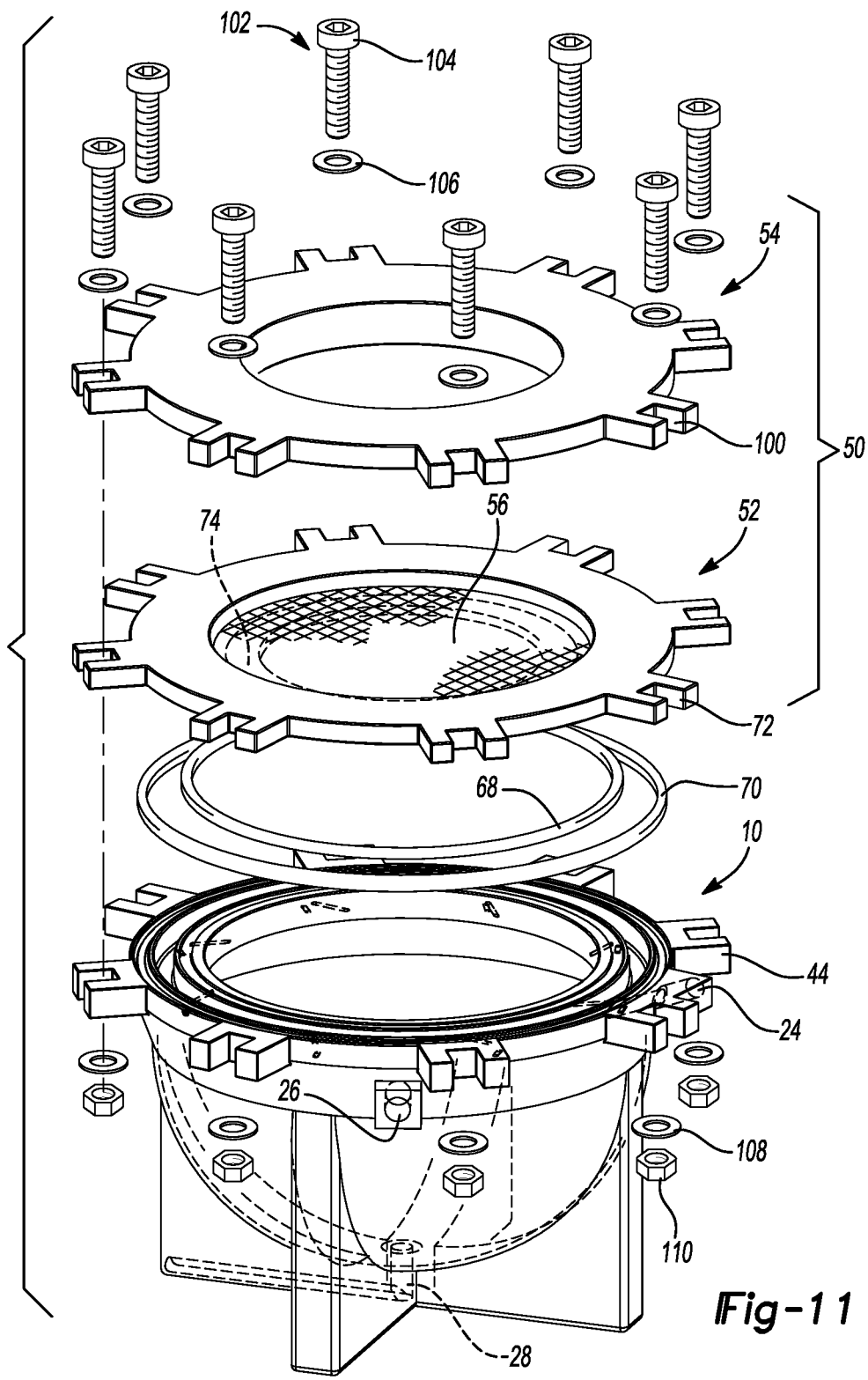
FIG. 11 is an exploded perspective view of the first device for washing a suspension of cells and lower and upper lid units.

FIG. 11 shows an exploded view of the device 10 and the lid assembly 50. As described above, the lower lid unit 52 is placed on top of the device 10, with the first O-ring 68 and second O-ring 70 of the lower unit 52 mating with the first groove 41 and second groove 42 of the device 10, respectively. Also, the plurality of second tabs 72 of the lower lid unit 52 align with the plurality of first tabs 44 of the device 10. The disc-shaped filter 56 is placed on the ledge/shelf 74 of the lower lid unit 52. The upper lid unit 54 is then placed on top of the lower lid unit 52, with the filter 56 being captured between the ledge/shelf 74 of the lower unit 52 and the flat shoulder surface 94 of the shoulder 88 of the upper lid unit 54. The plurality of third tabs 100 of the upper lid unit 54 align with the plurality of second tabs 72 of the lower lid unit 52, which align with the plurality of first tabs 44 of the device. A plurality of fasteners 102 are coupled to the tabs 100, 72, 44, which compress the lid assembly 50 against the device 10. As shown in the figure, the fasteners 102 comprise a bolt 104, a first washer 106, a second washer 108, and a nut 110. In alternative embodiments, the plurality of fasteners are bolts, washers, and nuts; latches; or clips and there are a sufficient number of tabs that define hooks, slots, U-shaped slots, or slits to compress the lid assembly 50 against the device 10.

Figure 12:
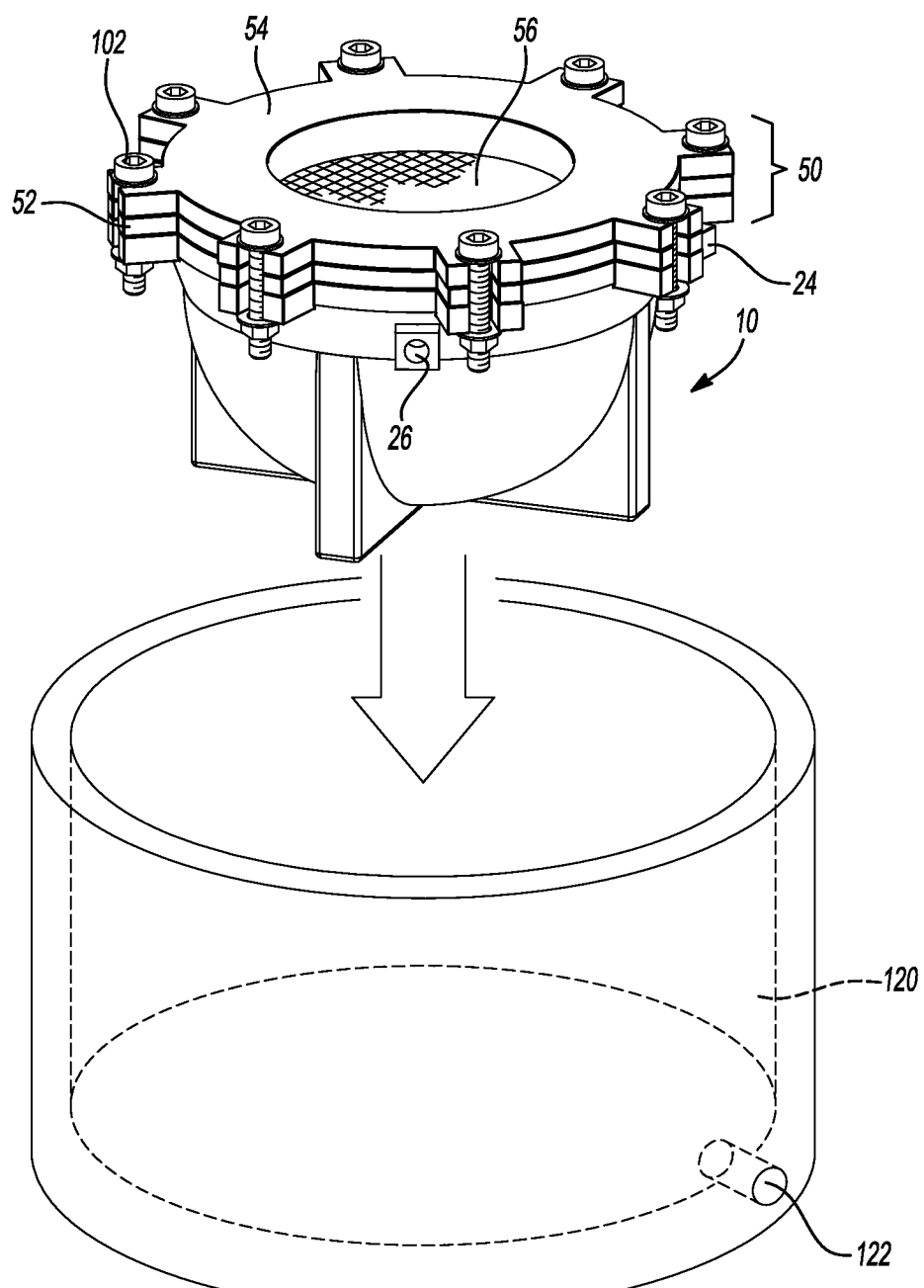
FIG. 12 is an assembled perspective view of the first device for washing a suspension of cells being lowered into a secondary basin.

FIG. 12 shows an assembled view of the device 10 with first inlet port 24 and second inlet port 26 and the lid assembly 50 comprising the lower lid unit 52, the filter 56, and the upper lid unit 54, wherein the lid assembly 50 is coupled to the device 10 by fasteners 102. The device 10 can be used to wash a suspension of cells, such as a suspension of red blood cells. The device 10 is placed into a secondary basin 120, which may or may not comprise a drain 122. When either inlet port 24, 26 is not in use, it should be capped. When wash solution is continuously injected or delivered through the first inlet port 24, it flows around the reservoir 30, through the angled apertures 40, and around the basin 12 about the central axis 22. When the device 10 is full, the wash solution overflows out through the filter 56, and into the secondary basin 120. The circular flow of wash solution around the basin 12 results in a vortex. When the device is full of circulating wash solution, the suspension of cells is injected or delivered into the vortex through the second inlet port 26. The filter 56 prevents the cells from escaping from the device 10 and the circular flow of wash solution helps prevent the filter 56 from getting clogged. The cells are washed as they enter circularly-flowing wash solution and the vortex forces them to settle at the bottom end 20 of the device 10. After all the cells have settled at the bottom end 20 of the device 10, the injection of wash solution can be stopped and the cells can be extracted. In one embodiment, the cells are extracted through the extraction port 28. In other embodiments, extracting the cells comprises removing the lid assembly 50, and removing the cells along with the wash solution through the first circular opening 38. Alternatively, extracting comprises selecting a syringe comprising a barrel, a plunger, and a cannula, inserting the cannula through the first circular opening 38, through the wash solution, and into the cells, and drawing back the plunger to aspirate the cells into the syringe barrel. In one embodiment, the device 10 is disposable.

Figure 13:
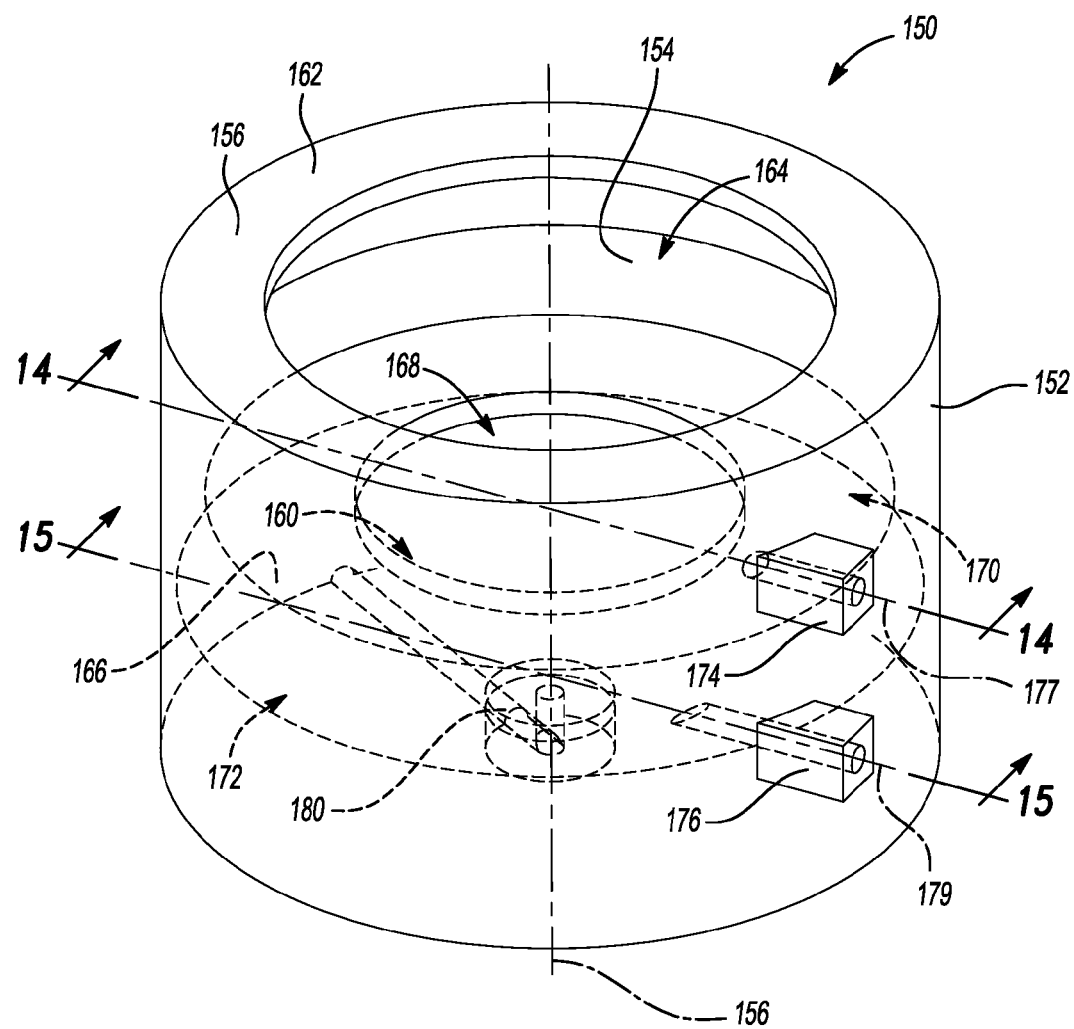
FIG. 13 is a perspective view of a second device for washing a suspension of cells.
Figure 14:
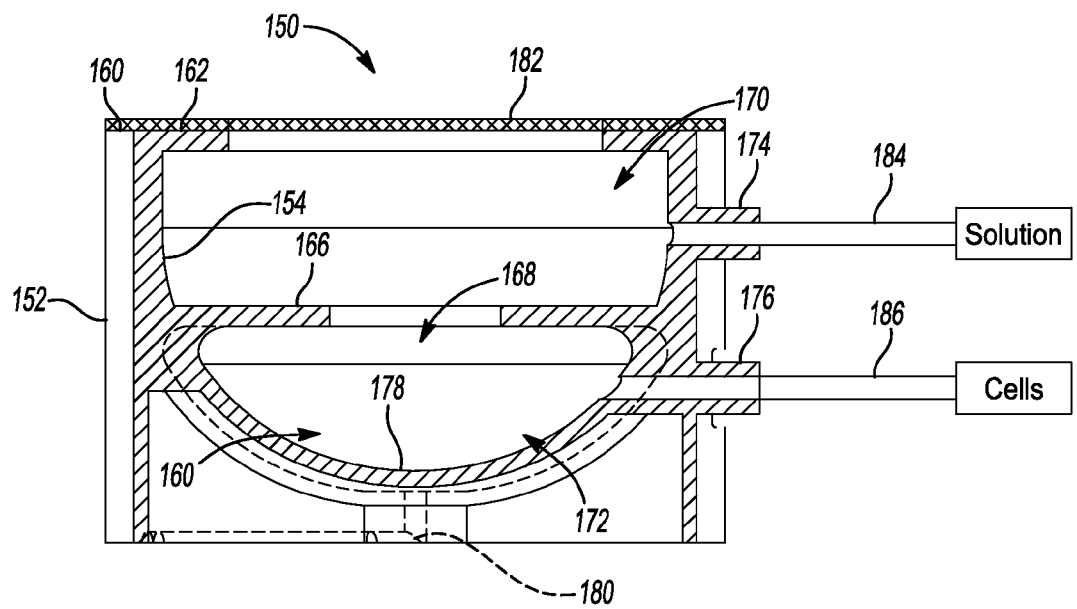
FIG. 14 is a cross section of a first configuration of the second device taken along line 14 of FIG. 13 for washing a suspension of cells.
Figure 15:
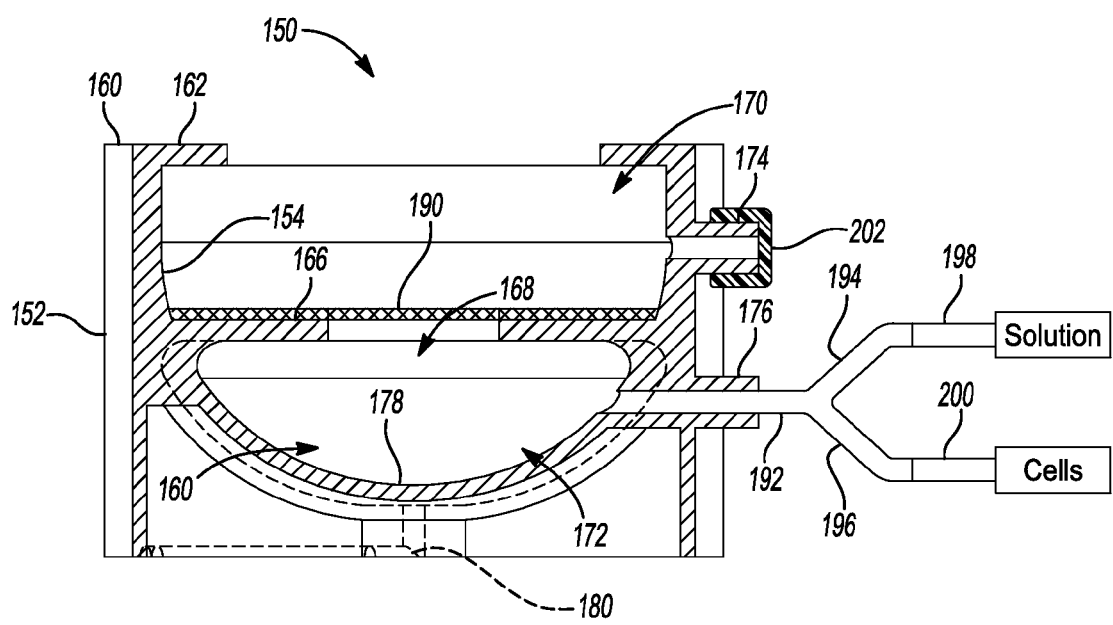
FIG. 15 is a cross section of a second configuration of the second device taken along line 15 of FIG. 13 for washing a suspension of cells.

With references to FIGS. 13-15, the present teachings further provide a device 150 for washing a suspension of cells that is manufactured as a single unit. The device 150 comprises a curved cylindrical outer surface 152, an inner surface 154, a top surface, 156, and a central axis 158, wherein the inner surface 154 defines a bowl-like basin 160. The top surface 156 comprises an annular lip 162 that defines a first circular opening 164. An annular ledge 166 extends radially inward from the inner surface 154 into the basin 160, which defines a second circular opening 168. Therefore, the ledge 166 splits the basin into an upper compartment or portion 170 and a lower compartment or portion 172. A first angled inlet port 174 is positioned between the ledge 166 and the top surface 156, and a second angled inlet port 176 is positioned between the ledge and a bottom surface 178 of the basin 160. The first and second inlet ports 174, 176 extend along a plane that is perpendicular to the axis 156 and extends along a second axis 177 and a third axis 179, respectively, that pass through a portion of the perimeter of the outer surface 152 of the device 150. The first and second inlet ports 174, 176 are angled both to promote a circular fluid path or vortex and to allow cells to be delivered to the circular fluid path. For example, a wash solution can be delivered through the first inlet 174 so that it enters the basin 160 alongside the inner surface 154, which results in the circular fluid path or vortex. The wash solution is not delivered toward the center of the basin 160. The cells can then be delivered through the second inlet port 176 in the direction of the flowing wash solution. An extraction port 180 is located at the bottom surface 178 of the basin 160. When either of the inlets 174, 176 are not in use, then they can be capped. In some embodiments, the device 150 is a single, one-piece integrated unit with a monolithic basin 160.

Cross sections of the device 150 are shown in FIGS. 14-15, which show two different configurations. In a first configuration, FIG. 14, the device 150 comprises a first disc-shaped filter 182 that covers the first opening 164. The first filter 182 is coupled to the device 150 at the lip 162. In this embodiment, a first tubing 184 can be used to continuously inject a wash solution through the first angled inlet port 174. As the wash solution is continuously injected or delivered through the first inlet port 174 and into the upper compartment 170 of the device 150, the angle of the first inlet port 174 causes the wash solution to circulate around the basin 160 about axis 156. The circulating wash solution flows through the second opening 168 and into the lower compartment 172, where the circulating wash solution 186 forms a vortex. As the device 150 becomes full, wash solution overflows out of the device 150, through the filter 182. Moreover, the circulating wash solution helps to prevent the filter 182 from getting clogged. Therefore, the device 150 can be placed in a secondary basin, such as the secondary basin 120 depicted in FIG. 12. When the device 150 is full of wash solution, a suspension of cells can be injected or delivered into the wash basin 160 through a second tubing 186 and the second angled inlet port 176. The filter 182 prevents cells from escaping the device 150. The cells are washed as they enter circularly-flowing wash solution and the vortex forces them to settle at the bottom surface 178 of the device 150. After all the cells have settled at the bottom surface 178 of the device 150, the injection of wash solution can be stopped and the cells can be extracted through the extraction port 180. In one embodiment, the device 150 is disposable.

FIG. 15 shows the second configuration for the device 150. In this configuration, the device 150 comprises a second disc-shaped filter 190 that covers the second circular opening. The second filter 182 is coupled to the device 150 at the ledge 166. In this embodiment, a y-adapter 192 comprising a first channel 194 and a second channel 196 is inserted into the second angled inlet port 176. Therefore, a third tubing 198 can inject a wash solution into the basin 160, and a fourth tubing 200 can inject a suspension of cells into the basin 160. In this embodiment, the first inlet port 174 is capped by a cap 202. When wash solution is continuously injected or delivered through the y-adapter 192 and into the basin 160 of the device 150, the angle of the second inlet port 176 causes the wash solution to circulate around the basin 160 about axis 156, where it forms a vortex. As the device 150 becomes full, wash solution overflows out of the device 150, through the second filter 190 and out the first opening 164. Moreover, the circulating wash solution helps to prevent the second filter 190 from getting clogged. Therefore, the device 150 can be placed in a secondary basin, such as the secondary basin 120 depicted in FIG. 12. When the device 150 is full of wash solution, the suspension of cells can be injected or delivered through the fourth tubing 200, through the y-adapter 192, through the second angled inlet port 176, and into the wash basin 160. The second filter 190 prevents cells from escaping the device 150. The cells are washed as they enter circularly-flowing wash solution and the vortex forces them to settle at the bottom surface 178 of the device 150. After all the cells have settled at the bottom surface 178 of the device 150, the injection of wash solution can be stopped and the cells can be extracted through the extraction port 180. In one embodiment, the device 150 is disposable.

Figure 16:
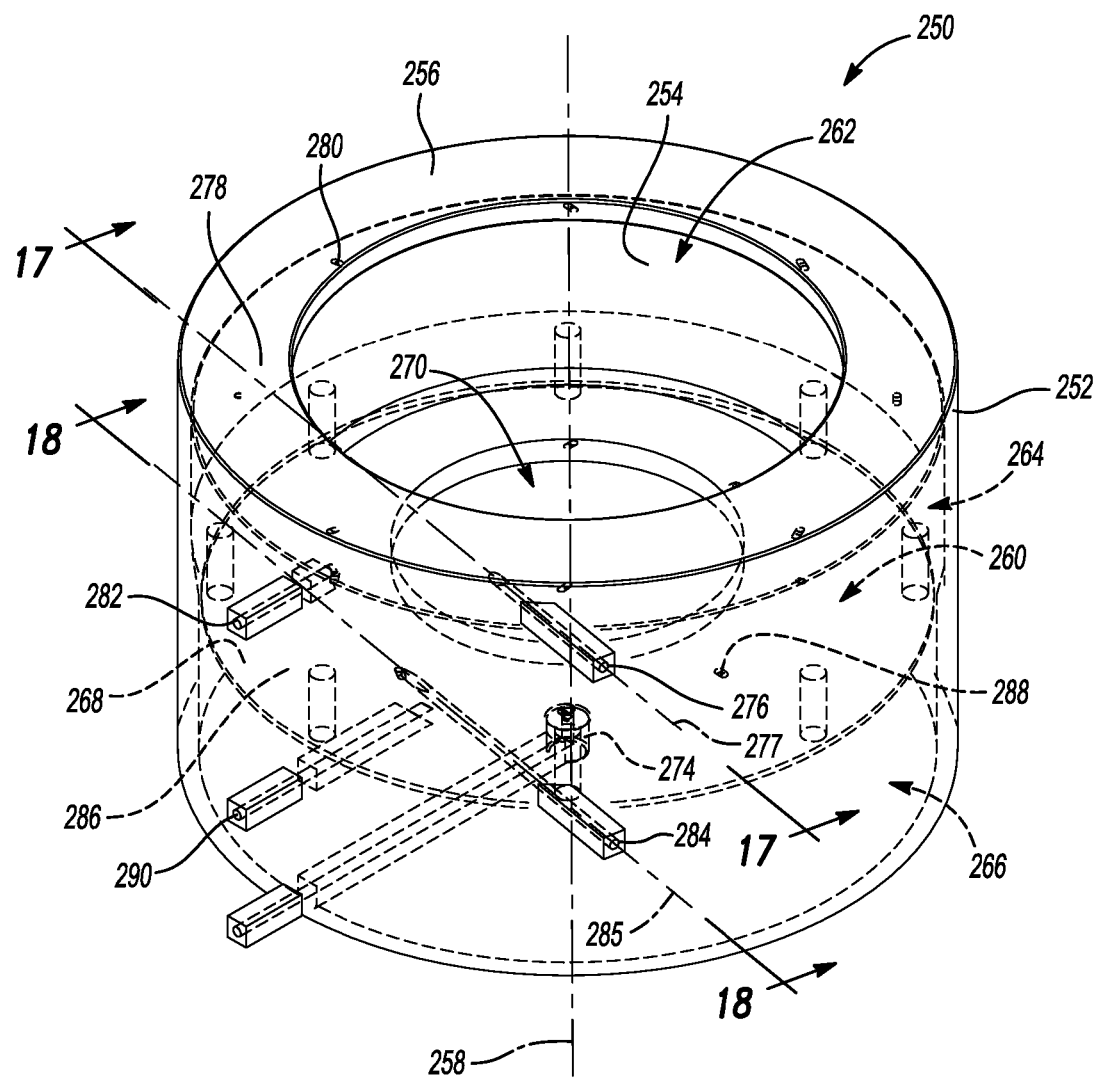
FIG. 16 is a perspective view of a third device for washing a suspension of cells.
Figure 17:
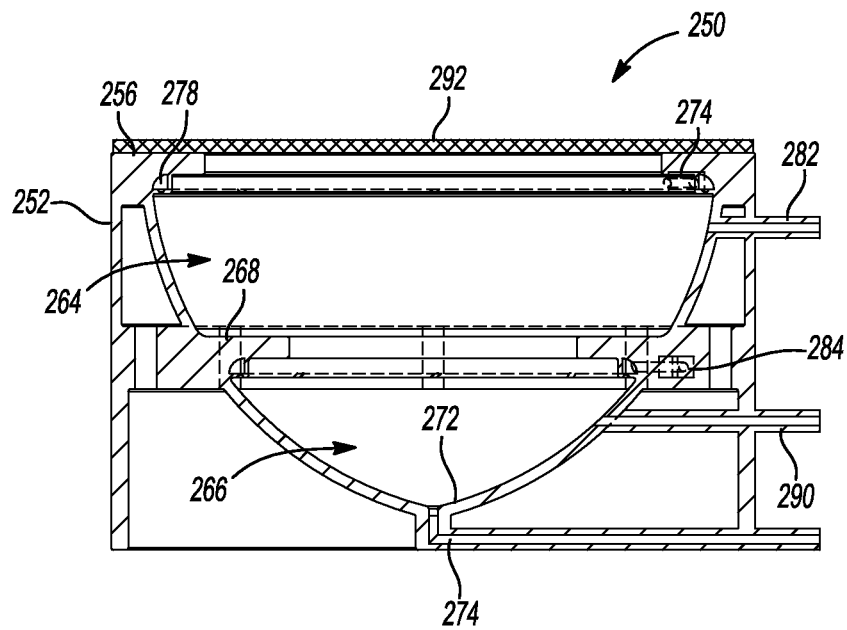
FIG. 17 is a cross section of a first configuration of the third device taken along line 17 of FIG. 16 for washing a suspension of cells.
Figure 18:
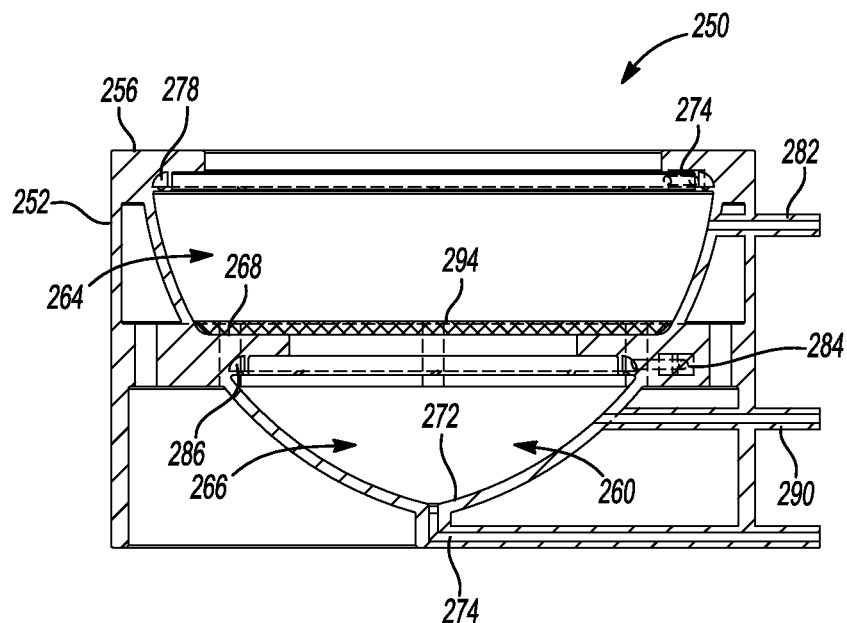
FIG. 18 is a cross section of a second configuration of the third device taken along line 18 of FIG. 16 for washing a suspension of cells.

With references to FIGS. 16-18, the present teachings also provide a third device 250 for washing a suspension of cells that is manufactured as a single unit. The device 250 comprises a curved cylindrical outer surface 252, an inner semi-spherical surface 254, a top annular surface, 256, and a central axis 258, wherein the inner surface 254 defines a bowl-like basin 260. The top annular surface 256 defines a first circular opening 262. The device further comprises an upper first compartment 264 and a lower second compartment 266, wherein the compartments 264,266 are separated by a ledge 268 that defines a second circular opening 270. The basin 260 comprises a lower surface 272, and an extraction port 274 is coupled to the lower surface 272 at the apex. In some embodiments, the device 250 is a single, one-piece integrated unit with a monolithic basin 260.

The device 250 further comprises an upper angled inlet port 276. The upper angled inlet port 276 extends along a plane that is perpendicular to the axis 258 and extends along a second axis 277 that passes through a portion of the perimeter of the cylindrical outer surface 252 of the device 250 to direct a clockwise flow of wash solution. In one embodiment a device has a configuration that is a mirror image of the device 250, in which flow of wash solution is directed in a counter-clockwise direction. An upper annular reservoir 278 is coupled to the device 250 so that solution being injected or delivered into the device 250 through the upper inlet port 276 directly enters the upper reservoir 278 and circulates around the upper reservoir 278. The upper reservoir 278 comprises a plurality of first radially positioned angled apertures 280, which encourage flowing solution to flow through the apertures and circulate in the compartments 264, 266 about the axis 258. In various embodiments, the first angled apertures 280 can be in a bottom surface of the upper reservoir 278, in a side surface of the upper reservoir 278, or both. In various embodiments, the device 250 comprises from about 2 angled apertures 280 to about 50 angled apertures 280. A second inlet port 282 is positioned below the upper reservoir 278, but above the ledge 268, and generally perpendicular to axis 258 and intersecting axis 258.

The device 250 further comprises a lower angled inlet port 284. The lower angled inlet port 284 extends along the plane that is perpendicular to the axis 258 and extends along a third axis 285 that passes through a portion of the perimeter of the cylindrical outer surface 252 of the device 250 to direct a clockwise flow of wash solution. In one embodiment, a device has a configuration that is a mirror image of the device 250, in which flow of wash solution is directed in a counter-clockwise direction. In any embodiment, the lower angled inlet port 284 is in a corresponding configuration as the upper angled inlet port 276, so that the inlet ports 284, 276 direct flow in the same direction. A lower annular reservoir 286 is coupled to the device 250 so that solution being injected or delivered into the device 250 through the lower inlet port 284 directly enters the lower reservoir 286 and circulates around the lower reservoir 286. The lower reservoir 286 comprises a plurality of second angled apertures 288, which encourage flowing solution to flow through the apertures and circulate in the lower compartment 266. In various embodiments, the second angled apertures 288 can be in a bottom surface of the lower reservoir 286, in a side surface of the lower reservoir 286, or both. A fourth inlet port 290 is positioned below the lower reservoir 286, but above the lower surface 272, and generally perpendicular to axis 258 and intersecting axis 258.

The cross section view of the device 250 shown in FIG. 17 shows a first embodiment. Here, a disc-shaped upper filter 292 is coupled to the top surface 256 of the device 250, which covers the first circular opening 262. In this embodiment, a wash solution can be continuously injected or delivered into the upper reservoir 278 through the upper angled inlet port 276. The wash solution flows through the first angled apertures 280 and into the compartments 264, 266 in a circular motion. The circular motion of the wash solution results in a vortex. When the device 250 is full of wash solution, the wash solution overflows out of the device 250, through the upper filter 292. Moreover, the circular motion of the wash solution helps to prevent the upper filter 292 from getting clogged. Therefore, the device 150 can be placed in a secondary basin, such as the secondary basin 120 depicted in FIG. 12. When the device 250 is full of wash solution, a suspension of cells, such as a suspension of red blood cells, can be injected or delivered through either the second inlet port 282 or through the fourth inlet port 290. The upper filter 292 prevents cells from escaping the device 250. Any inlet port 276, 282, 284, 290 that is not in use, can be capped. The cells are washed as they enter circularly-flowing wash solution and the vortex forces them to settle at the lower surface 272 of the device 250. After all the cells have settled at the lower surface 272 of the device 250, the injection of wash solution can be stopped and the cells can be extracted through the extraction port 274. In one embodiment, the device 250 is disposable.

The cross section view of the device 250 shown in FIG. 18 shows a second embodiment. Here, a disc-shaped lower filter 294 is coupled to the ledge 268 of the device 250, which covers the second circular opening 270. In this embodiment, a wash solution can be continuously injected or delivered into the lower reservoir 286 through the lower angled inlet port 284. The wash solution flows through the second angled apertures 288 and into the lower compartment 266 in a circular motion. The circular motion of the wash solution results in a vortex. When the device 250 is full of wash solution, the wash solution overflows out of the device 250, through the lower filter 294 and out through the first circular opening 262. Moreover, the circular motion of the wash solution helps to prevent the lower filter 294 from getting clogged. Therefore, the device 150 can be placed in a secondary basin, such as the secondary basin 120 depicted in FIG. 12. When the device 250 is full of wash solution, a suspension of cells, such as a suspension of red blood cells, can be injected or delivered through the fourth inlet port 290. The lower filter 294 prevents cells from escaping the device 250. Any inlet port 276, 282, 284, 290 that is not in use can be capped. The cells are washed as they enter circularly-flowing wash solution and the vortex forces them to settle at the lower surface 272 of the device 250. After all the cells have settled at the lower surface 272 of the device 250, the injection of wash solution can be stopped and the cells can be extracted through the extraction port 274. In one embodiment, the device 250 is disposable.

The present technology also provides methods for washing a suspension of cells. In various embodiments, the methods can be performed at a point of care. For example, the present technology provides methods where the washing of a suspension of cells is performed at a time proximate to administering the cells to a subject. For example, such proximate administration of the processed biological material may be performed 1 hour, 30 minutes, 15 minutes, 10 minutes, 2 minutes, 1 minute, or less, after obtaining a suspension of cells. The suspension of cells can be obtained from a donor, or the suspension of cells can be obtained from storage. Where lyophilized cells are obtained from storage, the cells can be suspended in any solution commonly used in the art, such as, for example, saline. In some processes, the methods are "point of care," wherein the processes of the present technology are performed at a location proximate, such as in the same room (for example, bed side) or otherwise immediately adjacent, to the subject undergoing treatment. In one embodiment, the suspension of cells is autologous to the subject to whom they will be administered. In other embodiments, the method is performed at a time prior to when the cells are to be administered to a subject.

In various embodiments, the method for washing a suspension of cells comprises continuously delivering a wash solution through a first inlet port and into an annular reservoir, wherein the wash solution flows through angled apertures and into a wash basin in a circular motion that results in a vortex. The wash solution can be any wash solution commonly used in the art. Non-limiting examples of wash solution include saline, phosphate buffered saline (PBS), and water. The method further comprises injecting a suspension of cells through a second inlet port, wherein the cells are dispersed in the solution and then settle at a bottom of the wash basin due to the downward force supplied by the vortex. The wash solution continuously flows through a filter when the wash basin is full, wherein the filter retains the cells in the wash basin. In some embodiments, the suspension of cells comprises red blood cells. The method then comprises extracting the cells.

Extracting the cells is performed after a predetermined amount of cells has been injected or delivered through the second inlet port and washed in the wash solution. After the predetermined amount of cells has been injected or delivered, the wash solution continues to be injected or delivered into the first inlet port for a period of time sufficient for all the cells to settle at the bottom of the wash basin. In various embodiments, the wash solution continues to be injected or delivered into the first inlet port for about 10 second, about 30 seconds, about 60 seconds, about 2 minutes, about 5 minutes, about 10 minutes, about 15 minutes, about 20 minutes, about 30 minutes, about 45 minutes, or about 60 minutes after the predetermined amount of cells has been injected or delivered.

In one embodiment, extracting comprises selecting a syringe comprising a barrel, a plunger, and a cannula; inserting the cannula into the cells at the bottom of the wash basin; and drawing back the plunger to aspirate the cells into the syringe barrel. In another embodiment, the wash solution is also a solution in which the cells are to be resuspended. Therefore, the cells can be harvested from the basin along with the remaining wash solution. In some embodiments, a volume of the wash solution is removed by aspiration from the wash basin in order to obtain a desired final concentration of cells. The volume of wash solution being removed can be from 0% to 100% of the wash solution remaining in the basin after the wash. After the volume of wash solution has been removed, then the cells can be suspended in the remaining wash solution to generate a washed suspension of cells, which can be collected from the basin, for example, by aspiration. In yet another embodiment, extracting comprises drawing the cellular material out of the wash basin through an outlet port at the bottom of the wash basin.

In another embodiment, the current technology provides a method for washing a suspension of red blood cells. The method comprises obtaining a device for washing blood comprising a wash basin, a top end, a bottom end, a first inlet port, a second inlet port, and a filter at the top end; and continuously injecting a wash solution through the first inlet port and into the wash basin, wherein the wash solution flows around the wash basin in a circular motion that results in a vortex. The wash solution continuously flows through the filter when the wash basin is full. The wash solution can be any wash solution commonly used in the art. Non-limiting examples of wash solution include saline, phosphate buffered saline (PBS), and water. The method further comprises injecting a suspension of red blood cells through the second inlet port, wherein the red blood cells are dispersed in the vortex and then settle at a bottom of the wash basin; and extracting the red blood cells.

In one embodiment, the device further comprises an annular reservoir comprising a plurality of angled apertures, and injecting further comprises injecting the wash solution through the first inlet port and into the annular reservoir, wherein the wash solution circulates around the reservoir and flows through the plurality of angled apertures and into the wash basin. The angled apertures are angled in a manner that promotes flow of the wash solution in to the wash basin.

Extracting the red blood cells is performed after a predetermined amount of red blood cells have been injected or delivered through the second inlet port and washed in the wash solution. After the predetermined amount of red blood cells has been injected or delivered, the wash solution continues to be injected or delivered into the first inlet port for a period of time sufficient for all the red blood cells to settle at the bottom of the wash basin. In various embodiments, the wash solution continues to be injected or delivered into the first inlet port for about 10 second, about 30 seconds, about 60 seconds, about 2 minutes, about 5 minutes, about 10 minutes, about 15 minutes, about 20 minutes, about 30 minutes, about 45 minutes, or about 60 minutes after the predetermined amount of red blood cells has been injected or delivered.

In one embodiment, extracting the red blood cells comprises selecting a syringe comprising a barrel, a plunger, and a cannula; inserting the cannula into the red blood cells at the bottom of the wash basin; and drawing back the plunger to aspirate the red blood cells into the syringe barrel. In another embodiment, the wash solution is also a solution in which the red blood cells are to be resuspended. Therefore, the red blood cells can be harvested from the basin along with the remaining wash solution. In some embodiments, a volume of the wash solution is removed by aspiration from the wash basin in order to obtain a desired final concentration of red blood cells. The volume of wash solution being removed can be from 0% to 100% of the wash solution remaining in the basin after the wash. After the volume of wash solution has been removed, the cells can be suspended in the remaining wash solution to generate a washed suspension of red blood cells, which can be collected from the basin, for example, by aspiration. In yet another embodiment, extracting comprises drawing the red blood cells out of the wash basin through an outlet port at the bottom of the wash basin.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for washing a suspension of cells comprising:
    a bowl-shaped basin having an inner surface, an outer surface, an open top end, a bottom end, and a central axis extending from the top end to the bottom end;
    an inlet port formed into the basin for continuously delivering a wash solution into the basin to fill the basin such that the wash solution overflows from the open top end, the inlet port being angled such that the wash solution circulates around the basin about the central axis, wherein the bowl-shaped basin maintains circular flow of the wash solution about the central axis, wherein a suspension of cells can be delivered into the circulating wash solution, and wherein the circulating wash solution forces the cells to settle at the bottom of the basin where the cells can be extracted;
    a filter at the top end permitting passage through the open top end of overflowing wash solution and retaining cells within the basin; and
    a lid assembly comprising an annular lower unit and an annular upper unit, wherein the filter is positioned between the lower unit and the upper unit.

2. The device according to claim 1, further comprising an annular reservoir that extends around the inner surface of the device at the top end, wherein the reservoir comprises a plurality of first angled apertures passing through the reservoir to deliver the wash solution to the basin, and wherein the inlet port directs the flow of wash solution into the reservoir.

3. The device according to claim 2, wherein the reservoir comprises a first wall, a second wall; and a bottom surface and the first angled apertures are on the bottom surface of the reservoir and promote a circular and downward flow of wash solution into the basin from the reservoir.

4. The device according to claim 3, wherein the annular reservoir further comprises a plurality of second angled apertures passing through the first wall of the reservoir, wherein the second angled apertures promote circular flow of wash solution into the basin from the reservoir.

5. The device according to claim 2, further comprising a second inlet port positioned below the reservoir, through which the suspension of cells can be delivered into the basin.

6. The device according to claim 5, wherein the suspension of cells comprises red blood cells.

7. The device according to claim 1, further comprising an outlet port positioned at the bottom end of the basin.

8. The device according to claim 1, wherein the lower lid unit comprises a plurality of O-rings that prevent wash solution or cells from leaking from between the device and the lid assembly.

9. The device according to claim 8, wherein the lower unit comprises a ledge in a central circular opening on which the filter is positioned.

10. The device according to claim 9, wherein the upper lid unit comprises an annular shoulder that presses down on the filter to secure the filter between the ledge of the lower lid unit and the shoulder of the upper lid unit.

11. The device according to claim 10, wherein the top end of the basin, the lower lid unit, and the upper lid unit have tabs that project outwardly and that are aligned with each other for accepting a plurality of fasteners for removably coupling the lid assembly to the top end of the basin.

12. The device according to claim 11, wherein the fasteners comprise nuts, washers, and bolts; latches; or clips.

13. The device according to claim 1, wherein the basin has an upper semi-spherical compartment, a lower semi-spherical compartment, and a ledge between the upper and lower semi-spherical compartments that extends radially inward.

14. The device according to claim 13, wherein the inlet port directs flow of the wash solution into the upper compartment, and wherein the device further comprises a second inlet port positioned below the ledge.

15. The device according to claim 14, further comprising a filter on one of the top end of the basin or the ledge.

16. The device according to claim 15, wherein the wash solution is delivered through the inlet port and into the basin and the suspension of cells is delivered through the second inlet port and into the basin when the filter is on the top end of the basin.

17. The device according to claim 15, wherein the wash solution and cells are delivered into the lower compartment of the basin through the second inlet port when the filter is on the ledge.

18. The device according to claim 15, further comprising a first annular reservoir that extends around the inner surface of the device at the top end, wherein the inlet port directs the flow of wash solution into and around the first reservoir, and a second annular reservoir that extends around the inner surface of the device below the ledge, wherein the second inlet port directs the flow of wash solution into and around the second reservoir.

19. The device according to claim 18, wherein the first and second reservoirs comprise a plurality of evenly spaced apertures that direct the flow of wash solution in a circular flow to the upper compartment and lower compartment, respectively.

20. The device according to claim 19, further comprising a third inlet port positioned below the first reservoir and above the ledge, and a fourth inlet port positioned below the second reservoir, wherein the suspension of cells can be delivered into the upper or lower compartment through the third or fourth inlet port, respectively.

21. The device according to claim 15, wherein the device is a single unitary device.

22. A device for washing red blood cells comprising:
 a. a substantially bowl-shaped wash basin, comprising an open top end, a bottom end, and an annular reservoir, the annular reservoir having a plurality of angled apertures;
 b. an annular lid including a filter, wherein the annular lid is in contact with and covers the reservoir, and the filter covers the open top end of the wash basin;
 c. a first angled inlet port for continuously introducing a wash solution into the reservoir, wherein the angle of the inlet port directs wash solution to flow around the reservoir and through the angled apertures to fill the basin such that the wash solution overflows from the open top end and generate a vortex of wash solution in the basin; and
 d. a second inlet port for introducing the red blood cells into the wash basin, wherein the second inlet is positioned below the annular reservoir, wherein the filter retains the red blood cells within the basin as the wash solution overflows from the open top end.

23. The device according to claim 22, further comprising an outlet port positioned at the bottom of the bowl-shaped wash basin for extracting washed red blood cells.

24. The device according to claim 22, wherein the disc-shaped filter; the lid, and the wash basin are fabricated as a single disposable unit.

* * * * *